United States Patent
Searle et al.

(10) Patent No.: US 11,123,520 B2
(45) Date of Patent: Sep. 21, 2021

(54) COLLAPSE-RESISTANT SWELLABLE CATHETER

(71) Applicant: Becton, Dickinson and Company, Franklin Lakes, NJ (US)

(72) Inventors: Gary Searle, Norfolk, MA (US); Charles G. Hwang, Wellesley, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 197 days.

(21) Appl. No.: 16/251,494

(22) Filed: Jan. 18, 2019

(65) Prior Publication Data

US 2019/0151611 A1    May 23, 2019

Related U.S. Application Data

(63) Continuation of application No. 13/479,114, filed on May 23, 2012, now Pat. No. 10,220,186.

(51) Int. Cl.
*A61M 25/00* (2006.01)
*A61M 5/142* (2006.01)
*A61L 29/06* (2006.01)

(52) U.S. Cl.
CPC ......... *A61M 25/0045* (2013.01); *A61L 29/06* (2013.01); *A61M 5/142* (2013.01); *A61M 5/14248* (2013.01); *A61M 25/0009* (2013.01); *A61M 25/0043* (2013.01); *A61M 2025/0059* (2013.01); *A61M 2025/0065* (2013.01)

(58) Field of Classification Search
CPC .......... A61M 25/0045; A61M 5/14248; A61M 25/0043; A61M 25/0009; A61M 2025/0059; A61M 2025/0065
See application file for complete search history.

(56) References Cited

U.S. PATENT DOCUMENTS

| | | |
|---|---|---|
| 3,545,443 A | 12/1970 | Ansari |
| 4,044,119 A | 8/1977 | Carlson et al. |
| 4,141,364 A | 2/1979 | Schultze |
| 4,401,433 A | 8/1983 | Luther |
| 4,406,656 A | 9/1983 | Hattler et al. |

(Continued)

FOREIGN PATENT DOCUMENTS

| | | |
|---|---|---|
| CN | 102427846 A | 4/2012 |
| EP | 0341049 A2 | 11/1989 |

(Continued)

OTHER PUBLICATIONS

Lamba, N. M.K. et al., Polyurethanes in Biomedical Applications, CRC Press. 1998. p. 207.
BD Vialon Biomaterial. BD Medical, 2006.

*Primary Examiner* — Bradley J Osinski
(74) *Attorney, Agent, or Firm* — .Dickinson Wright PLLC

(57) ABSTRACT

An infusion system comprising a base, a pump, a fluid tubing set that connects the pump and the base, and a collapse-resistant catheter extending from the base and comprising a swellable inner element including one or more indents, and a non-swellable flexible outer sleeve covering an outer wall of the inner element, wherein when the swellable inner element absorbs liquid, the swellable inner element swells and the one or more indents control a direction of the swelling by causing the swellable inner element to fold inwardly.

20 Claims, 12 Drawing Sheets

(56) References Cited

U.S. PATENT DOCUMENTS

| | | | |
|---|---|---|---|
| 4,548,205 | A | 10/1985 | Armeniades et al. |
| 4,601,713 | A | 7/1986 | Fuqua |
| 4,681,561 | A | 7/1987 | Hood et al. |
| 4,693,249 | A | 9/1987 | Schenck et al. |
| 4,710,181 | A | 12/1987 | Fuqua |
| 4,776,846 | A | 10/1988 | Wells |
| 4,808,154 | A | 2/1989 | Freeman |
| 4,840,623 | A | 5/1989 | Quackenbush |
| 4,840,622 | A | 6/1989 | Hardy |
| 4,883,699 | A * | 11/1989 | Aniuk .................. A61L 29/049 428/36.9 |
| 4,935,017 | A | 6/1990 | Sylvanowicz |
| 4,954,129 | A | 9/1990 | Giuliani et al. |
| 4,994,047 | A | 2/1991 | Walker et al. |
| 5,112,301 | A | 5/1992 | Fenton et al. |
| 5,215,527 | A | 6/1993 | Beck et al. |
| 5,226,899 | A | 7/1993 | Lee et al. |
| 5,453,099 | A | 9/1995 | Lee et al. |
| 5,478,328 | A | 12/1995 | Silverman et al. |
| 5,505,693 | A | 4/1996 | Mackool |
| 5,545,708 | A | 8/1996 | Onwunaka et al. |
| 5,553,625 | A | 9/1996 | Rao |
| 5,599,306 | A | 2/1997 | Klein et al. |
| 5,674,240 | A | 10/1997 | Bonutti |
| 5,741,275 | A | 4/1998 | Wyssmann |
| 5,772,629 | A | 6/1998 | Kaplan |
| 5,814,020 | A | 9/1998 | Gross |
| 5,817,099 | A | 10/1998 | Skolik et al. |
| 5,840,008 | A | 11/1998 | Klein |
| 5,971,959 | A | 10/1999 | Liu |
| 6,106,515 | A | 8/2000 | Winston |
| 6,589,464 | B1 | 7/2003 | Dutta |
| 6,743,206 | B1 | 6/2004 | Smith et al. |
| 6,749,589 | B1 | 6/2004 | Douglas et al. |
| 7,637,902 | B2 | 12/2009 | Eversull |
| 7,713,281 | B2 | 5/2010 | Leeflang |
| 7,766,820 | B2 | 8/2010 | Core |
| 7,766,906 | B2 | 8/2010 | Swanson |
| 7,780,692 | B2 | 8/2010 | Nance |
| 7,806,865 | B1 | 10/2010 | Wilson |
| 7,875,049 | B2 | 1/2011 | Eversull |
| 7,892,203 | B2 | 2/2011 | Lenker |
| 7,892,216 | B2 | 2/2011 | Fangrow, Jr. |
| 7,905,877 | B1 | 3/2011 | Jimenez et al. |
| 8,070,711 | B2 | 12/2011 | Bassinger et al. |
| 8,100,881 | B2 | 1/2012 | Hoffa |
| 8,303,549 | B2 | 11/2012 | Mejihede et al. |
| 8,414,605 | B2 | 4/2013 | Gordon et al. |
| 8,690,936 | B2 | 4/2014 | Nguyen |
| 8,790,387 | B2 | 7/2014 | Nguyen |
| 9,821,140 | B2 | 11/2017 | Pini |
| 2002/0045852 | A1 | 4/2002 | Saab |
| 2002/0143292 | A1 | 10/2002 | Flinchbaugh |
| 2002/0183722 | A1 | 12/2002 | Harper et al. |
| 2004/0087968 | A1 | 5/2004 | Core |
| 2004/0143241 | A1 | 7/2004 | Douglas et al. |
| 2005/0137524 | A1 | 6/2005 | Sakai et al. |
| 2005/0226814 | A1 | 10/2005 | Levy |
| 2005/0261663 | A1 | 11/2005 | Patterson |
| 2006/0052750 | A1 | 3/2006 | Lenker |
| 2006/0100653 | A1 | 5/2006 | Akahoshi |
| 2006/0135962 | A1 | 6/2006 | Kick |
| 2007/0016165 | A1 | 1/2007 | Von Oepen et al. |
| 2007/0021648 | A1 * | 1/2007 | Lenker .............. A61M 25/0097 600/29 |
| 2007/0185454 | A1 | 8/2007 | Fangrow, Jr. |
| 2008/0009826 | A1 | 1/2008 | Miller et al. |
| 2008/0039792 | A1 | 2/2008 | Meng et al. |
| 2009/0054845 | A1 | 2/2009 | Puhasmagi et al. |
| 2009/0093789 | A1 | 4/2009 | Dacquay et al. |
| 2009/0287183 | A1 | 11/2009 | Bishop |
| 2010/0063438 | A1 * | 3/2010 | Bengtsson ........... A61B 5/0452 604/66 |
| 2010/0170619 | A1 | 7/2010 | Strong |
| 2011/0054285 | A1 | 3/2011 | Searle et al. |
| 2011/0054390 | A1 | 3/2011 | Searle et al. |
| 2011/0137231 | A1 | 6/2011 | Sorensen et al. |
| 2011/0306843 | A1 | 12/2011 | Lenker |
| 2011/0313357 | A1 | 12/2011 | Skutnik et al. |
| 2012/0065578 | A1 | 3/2012 | Zhou |
| 2012/0157934 | A1 | 6/2012 | Liao et al. |
| 2012/0172786 | A1 | 7/2012 | Mackool |
| 2012/0203198 | A1 | 8/2012 | Searle et al. |
| 2013/0317476 | A1 | 11/2013 | Searle et al. |

FOREIGN PATENT DOCUMENTS

| | | |
|---|---|---|
| JP | H02-63466 A | 3/1990 |
| JP | H07-93944 A | 10/1995 |
| WO | WO2010/080715 A1 | 7/2010 |
| WO | WO2011/081001 A1 | 7/2011 |

* cited by examiner

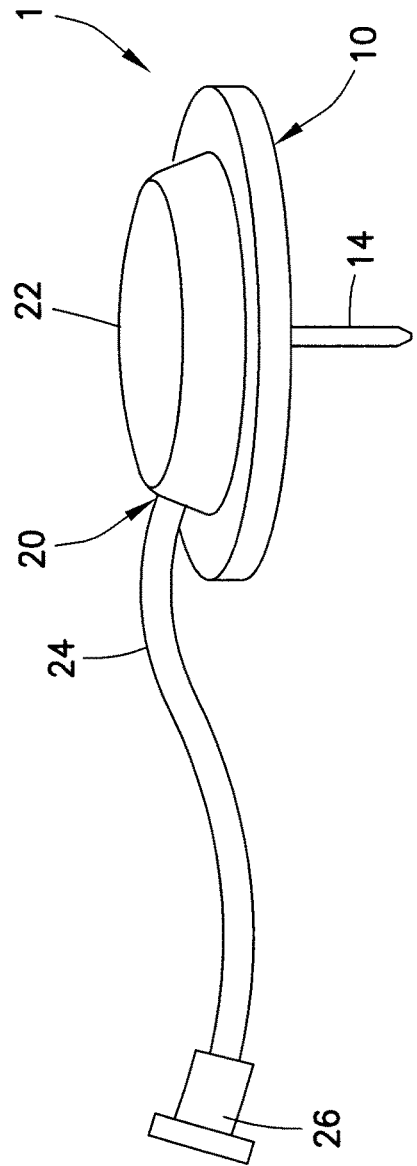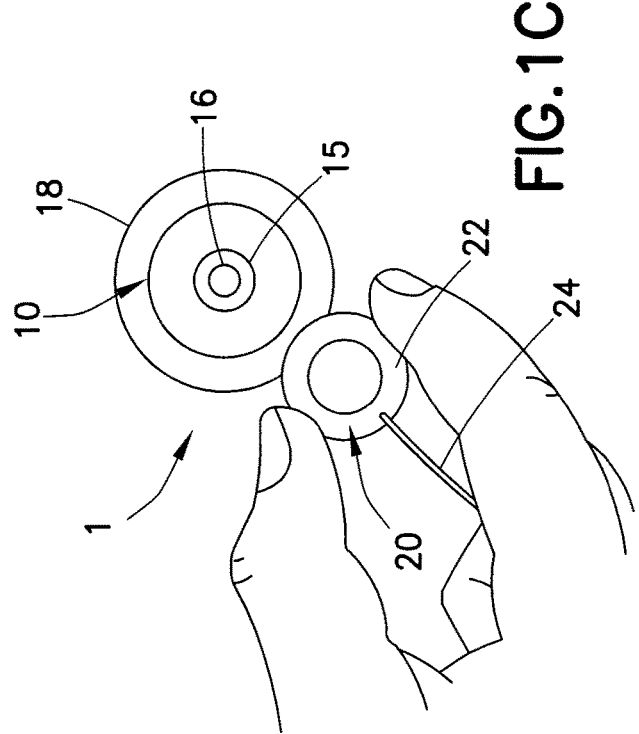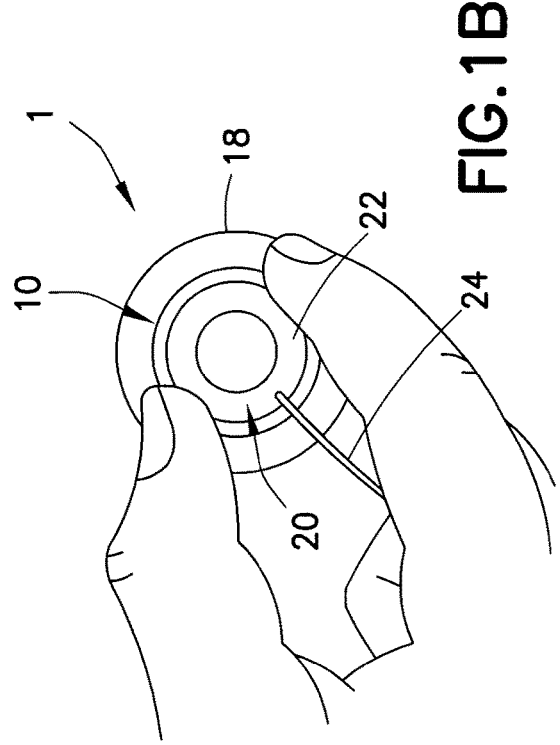

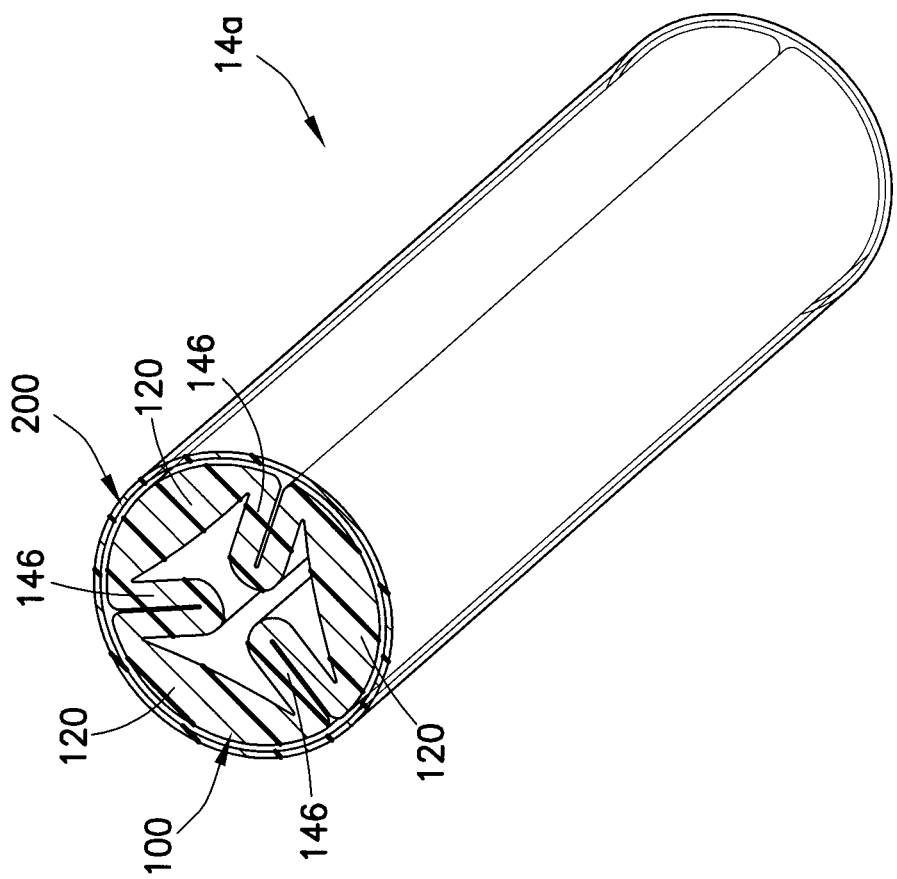
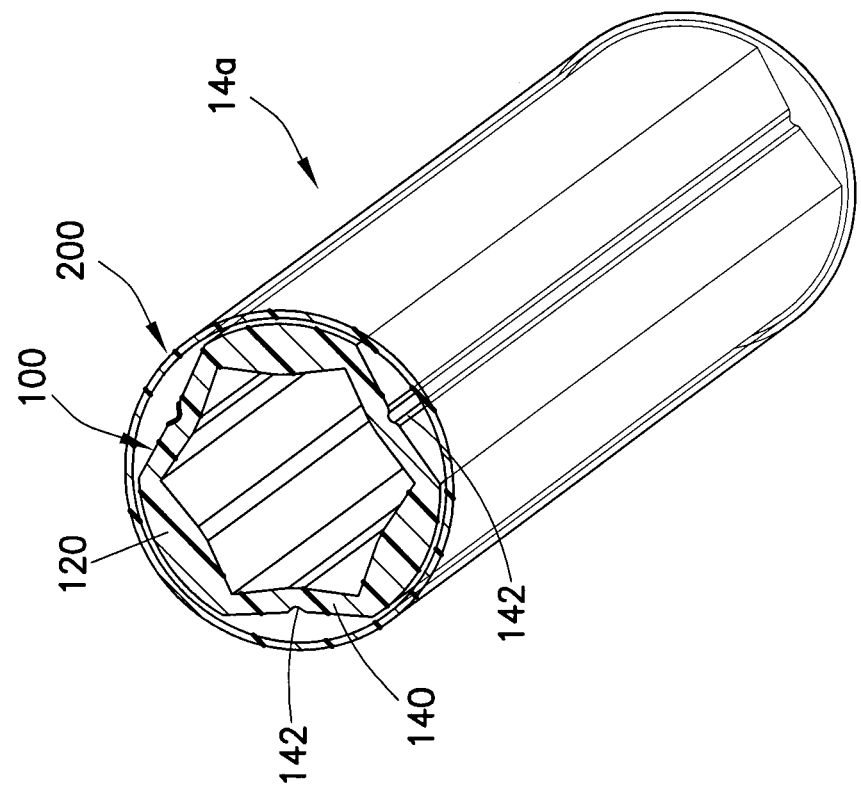

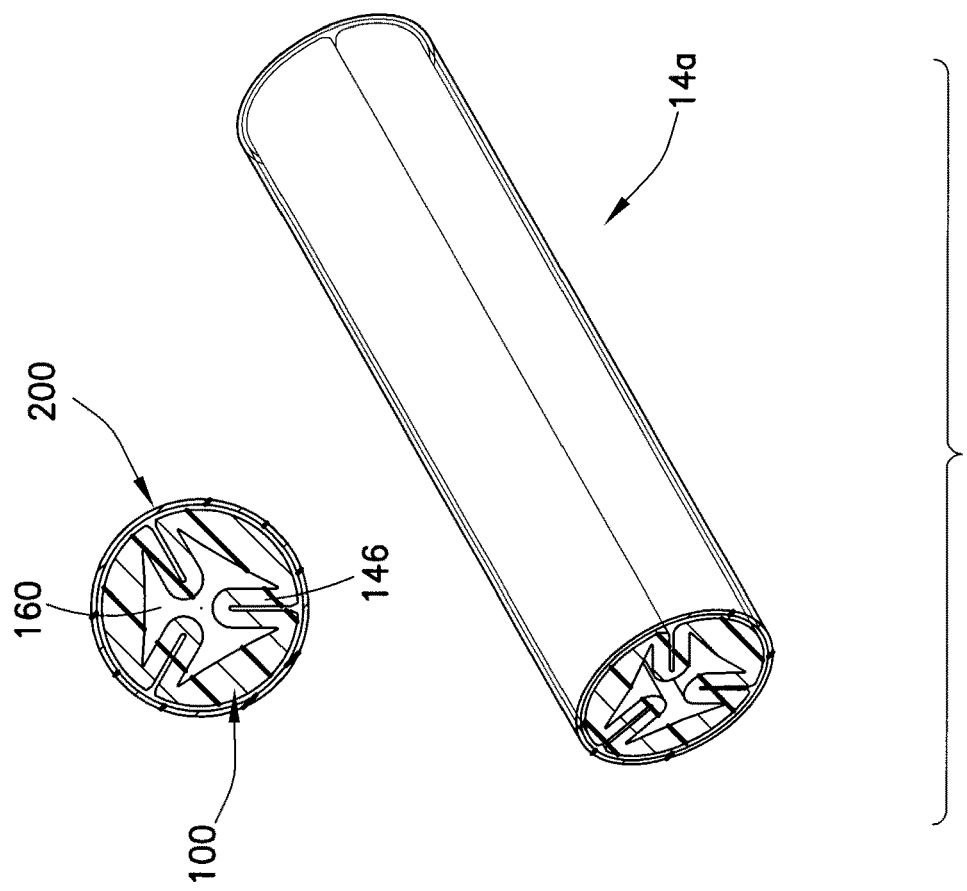
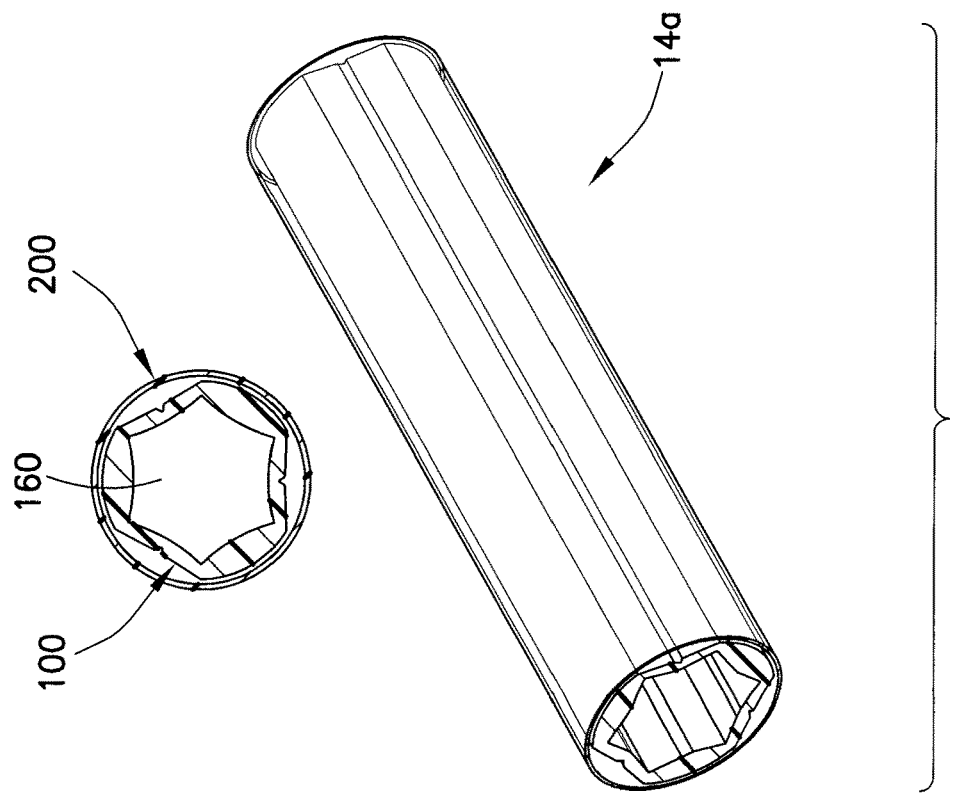

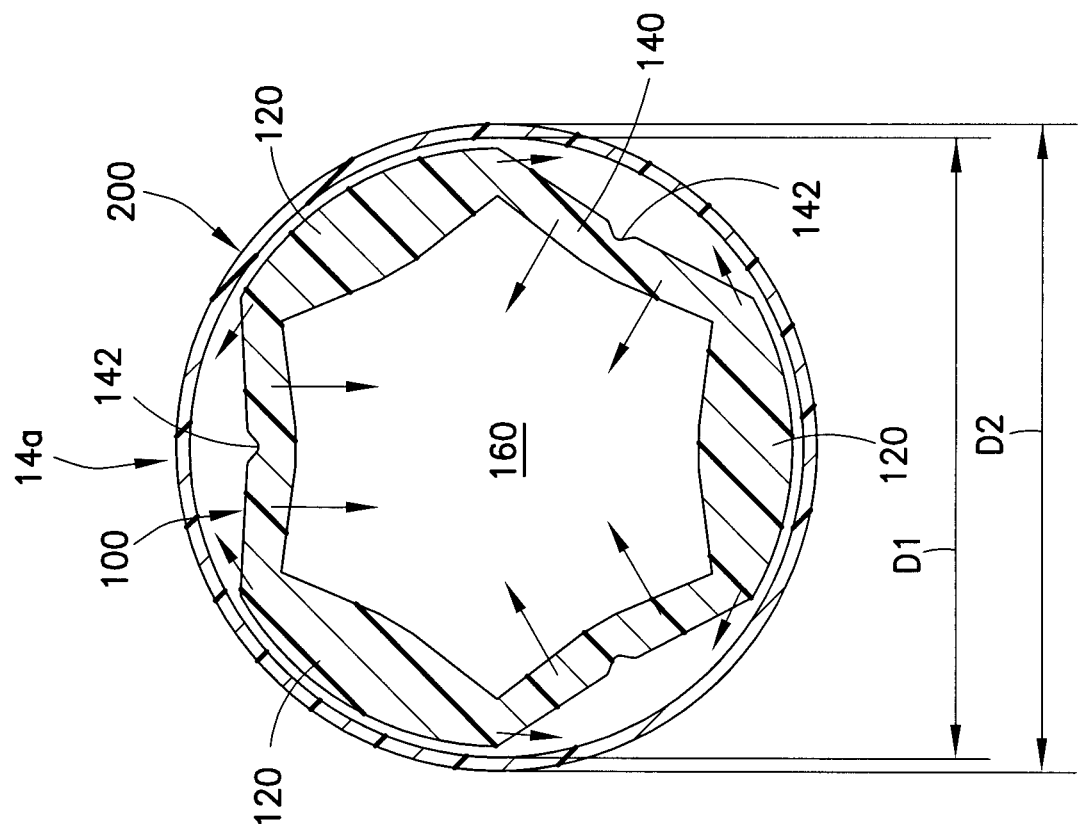
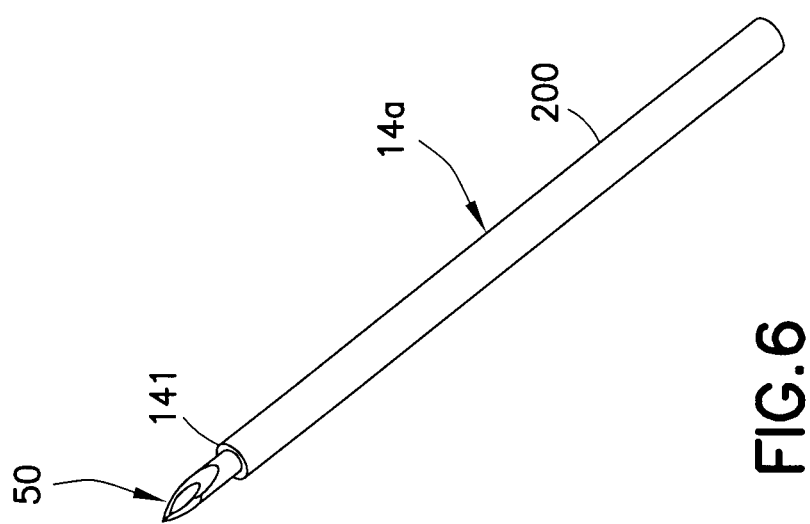

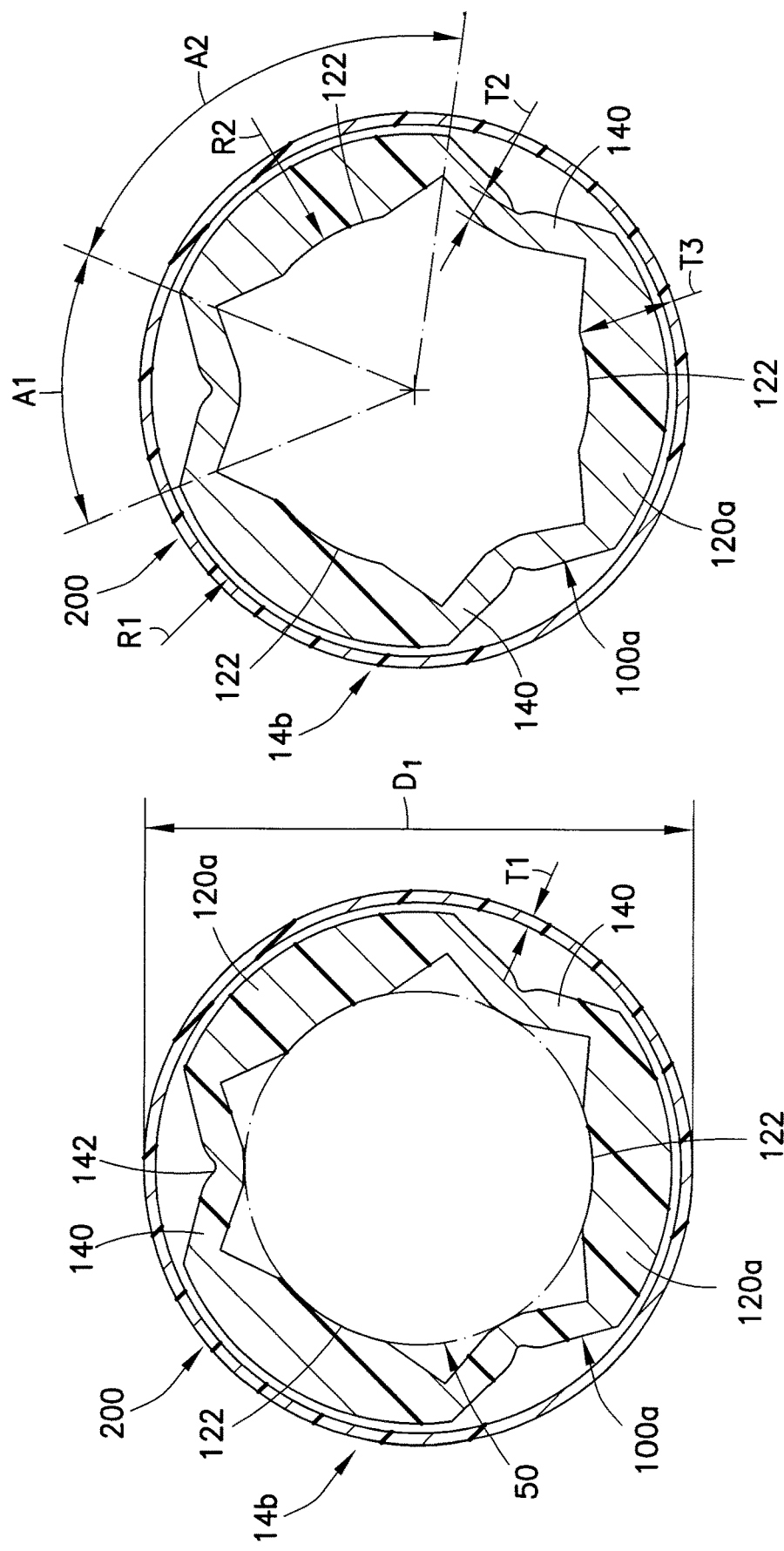

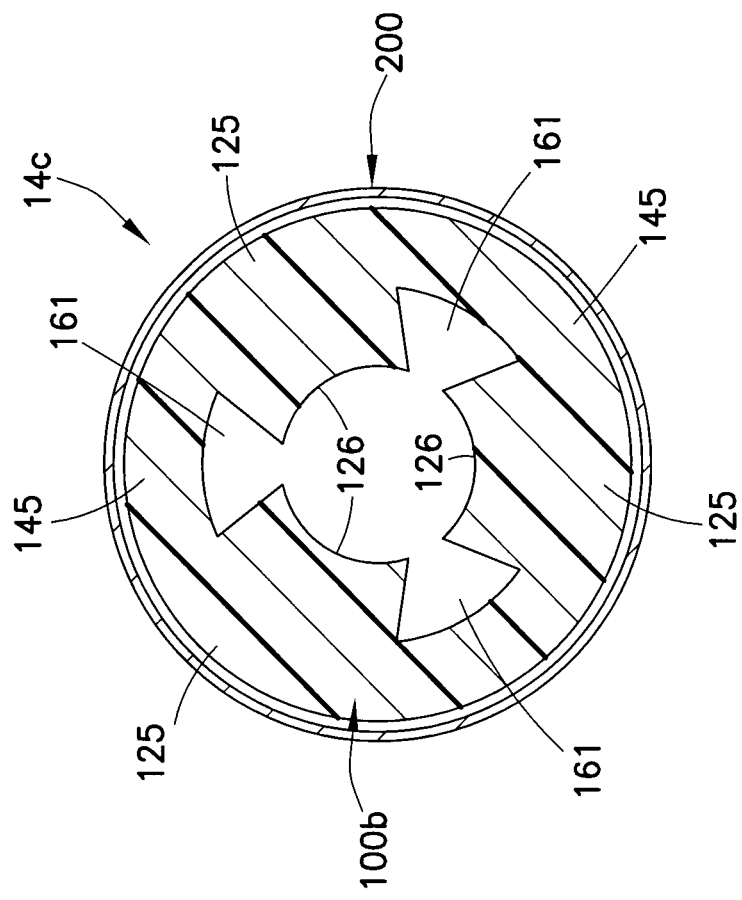
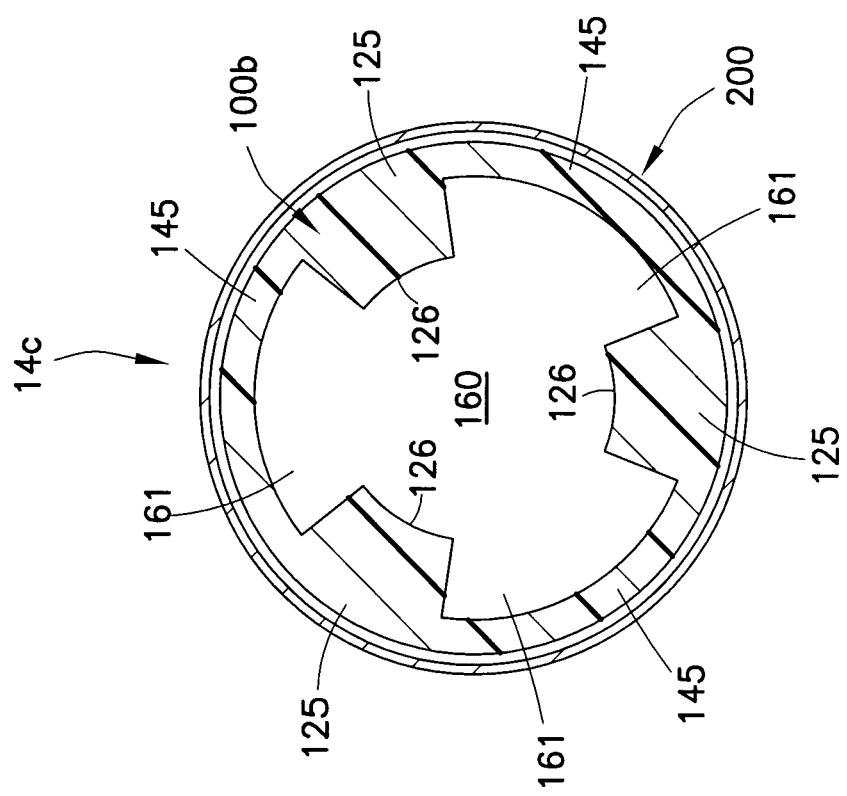

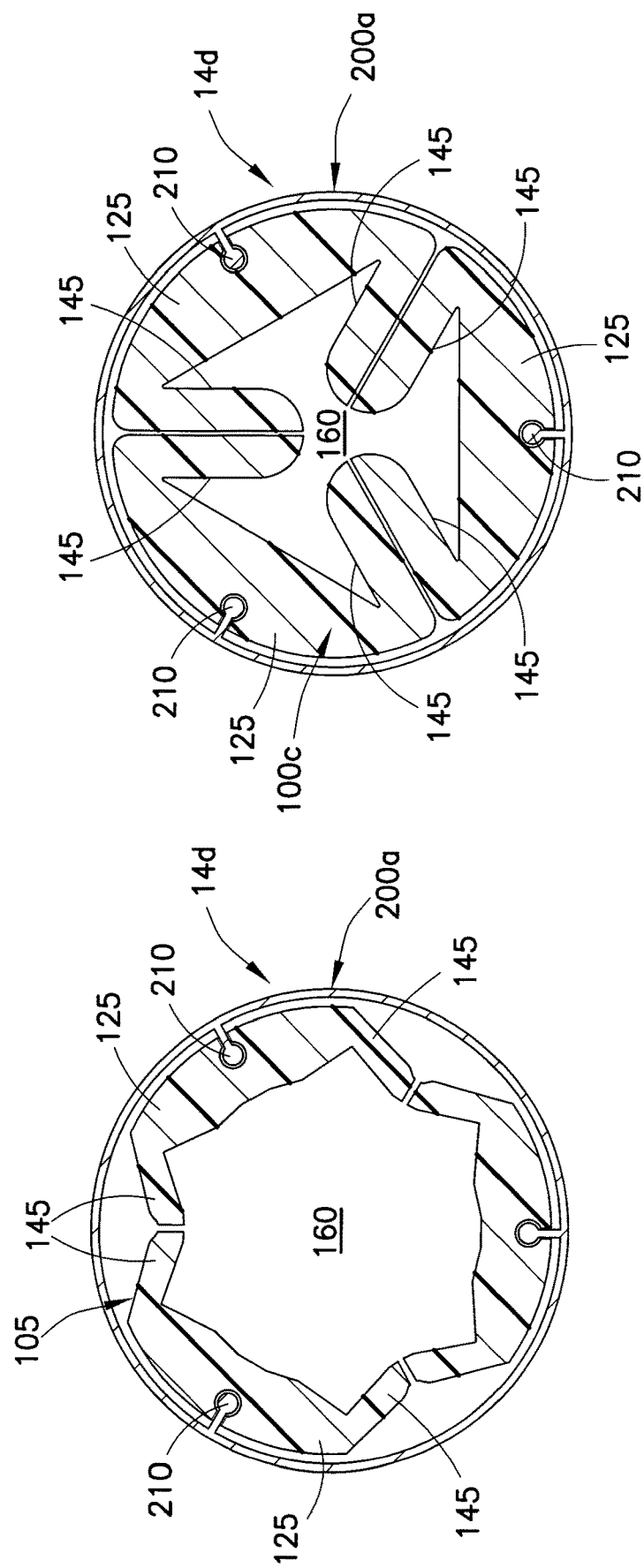

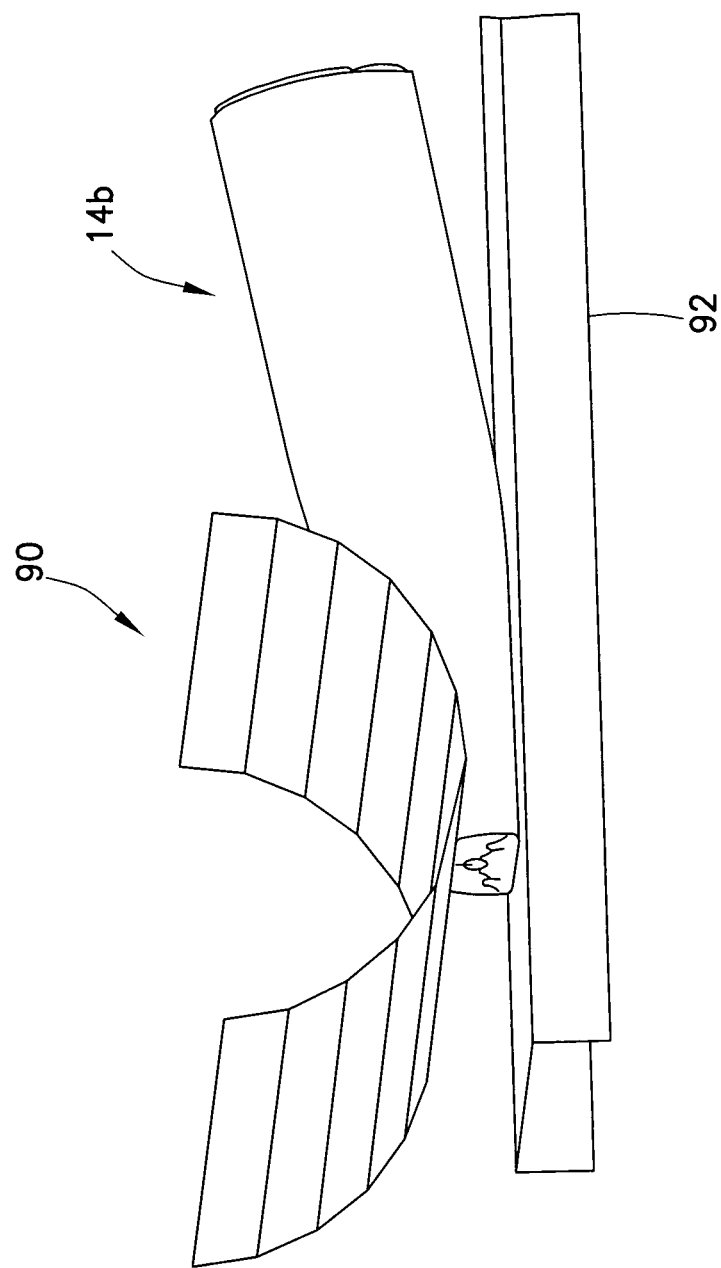

COLLAPSE-RESISTANT SWELLABLE CATHETER

RELATED APPLICATIONS

This application is a continuation of U.S. Nonprovisional Patent application Ser. No. 13/479,114, filed on May 23, 2012, which is incorporated herein by reference in its entirety.

FIELD OF THE INVENTION

The present invention relates generally to catheters and methods of manufacture thereof that improve the strength and functionality of the catheters.

BACKGROUND OF THE INVENTION

A large number of people with diabetes use some form of daily insulin therapy to maintain close control of their glucose levels. Currently, there are two principal modes of daily insulin therapy. The first mode includes syringes and insulin pens. These devices are simple to use and are relatively low in cost, but they require a needle stick at each injection, typically three to four times per day. The second mode includes infusion pump therapy, via an infusion cannula (i.e., an infusion needle or a flexible catheter), which requires an infusion pump. Infusion pumps, although more complex and expensive than syringes and pens, offer the advantages of continuous infusion of insulin, precision dosing, and programmable delivery schedules. This allows closer blood glucose control which can result in improved health outcomes.

The use of an infusion pump requires the use of a disposable component, typically referred to as an infusion set, tubing set or pump set, which conveys the insulin from a reservoir within the pump into the skin of the user. An infusion set typically consists of a pump connector, a length of tubing, and a hub or base from which an infusion needle or catheter extends. The base has an adhesive that retains the base on the skin surface during use. The base may be applied to the skin manually or with the aid of a manual or automatic insertion device. Often, the insertion device is a separate, stand-alone unit that the user is required to carry and provide.

There are many available types of infusion sets incorporating various types of infusion cannulas, including steel needle infusion sets and soft catheter sets. Soft catheter sets can be inserted into a patient manually with the aid of a steel introducer needle, which is later removed from the patient, leaving the soft catheter in place. Alternatively, a mechanized inserter can be used to insert the introducer needle and catheter, after which the introducer needle is removed. In either case, the introducer needle is completely removed from the infusion set before the infusion set is connected to the insulin pump.

Another type of insulin infusion device is a patch pump. Unlike a conventional infusion pump and infusion set combination, a patch pump is an integrated device that combines most or all of the fluid components (including the fluid reservoir and pumping mechanism) in a single housing which is adhesively attached to an infusion site, and does not require the use of a separate infusion (tubing) set. A patch pump adheres to the skin, contains insulin (or other medication), and delivers the insulin over a period of time via an integrated subcutaneous catheter. Some patch pumps communicate with a separate controller device wirelessly (as in one device sold under the brand name OmniPod®), while others are completely self-contained. These devices need to be reapplied on a frequent basis, such as every three days, when the reservoir is exhausted or as complications may otherwise occur.

FIG. 1A illustrates an infusion set 1 for use with an infusion cannula such as a catheter 14. As illustrated in FIG. 1A, the infusion set 1 comprises a fluid connector or hub 22 which is detachably attached to a base (10), a fluid tubing set 24 and a connector 26 which attaches to a pump (not shown). Line set 20 includes the hub 22 and the fluid tubing set 24 is attached to or detached from the base 10, as in FIGS. 1B and 1C.

FIG. 1B is a top view of the infusion set 1 with the hub 22 attached to the base 10. An adhesive pad 18 is attached to the base 10 and is configured to be attached to the skin of the user. FIG. 1C illustrates a view of the infusion set 1 when the line set 20 is detached from the base 10. The base 10 includes an infusion adapter 15 to which the catheter 14 is attached.

FIG. 1D is a cross-sectional view of the infusion set 1 and more clearly illustrates how the infusate is pumped into the catheter 14, which is preferably made of a soft plastic material. The hub 22 of the line set 20 includes a hub port 29 that receives the fluid tubing set 24. The hub 22 includes a flow cannula 23 and a fluid channel 28 positioned between the fluid tubing set 24 and the open tip 231 of the flow cannula 23. The base 10 includes a main base portion 12 to which the catheter 14 is secured. A pre-slit septum 16 encloses the adapter 15, when the hub 22 is detached from the infusion base 10, as illustrated in FIGS. 1C and 1E. When the hub 22 is attached to the base 10, the flow cannula 24 penetrates the pre-slit septum 16 so that the fluid channel 28 is in fluid communication with the catheter 14. This allows infusate from the pump (not shown) to flow from the fluid tubing set 24 into the fluid channel 28, and into the catheter 14, and the infusate exits the distal opening 141 of the catheter 14 into the patient.

Infusion cannulas for use in infusion sets and/or patch pumps are manufactured of either rigid material, such as stainless steel, or soft plastic materials, such as fluorinated polymers, including TEFLON® polymer. Infusion cannulas may be subject to kinking and occlusion.

A catheter can kink during or after insertion into a patient when the catheter tube becomes bent due to various causes, resulting in a restricted flow of infusate exiting the catheter. Kinking can be considered to be the cessation of flow through a catheter due to mechanical causes, such as bending of the catheter, sliding back or folding of the catheter on the introducer needle during insertion.

The restricted flow of the catheter can be caused by kinking and by other causes. In general, occlusion is the blockage or cessation of flow due to biological, pharmacological or mechanical causes, including kinking, and these failures typically occur during the use cycle.

Rigid catheters, such as stainless steel cannulas, may have a sharp tip, which is used to pierce the skin, similar to an introducer needle in a conventional inserter. Rigid catheters are recommended for individuals who experience a high incidence of kinking. However, such products are not recommended for use beyond two days, because they can reduce site patency, due to tissue irritation.

On the other hand, soft plastic catheters, such as the catheter 14 illustrated in FIG. 1D, may be prone to kink or occlude with normal wear, while rigid catheters (not shown) are often found to be uncomfortable to the user, since they tend to move around within the tissue.

In infusion devices, it is highly desirable to minimize the risks of catheter occlusion, kinking and other complications, while maintaining a degree of comfort to the user. Kinking and occlusion are described in detail below.

As noted above, kinking is considered to be the cessation of flow through a catheter due to mechanical causes. This failure mode can be the result of insufficient interference between the inner diameter of the catheter and the outer diameter of the introducer needle during insertion. In addition, kinking can occur if a blunt distal end of the catheter allows excess force to be transmitted to the catheter as the catheter initially penetrates the outer surface of the skin. Similarly, excessive bounce or vibration in the insertion mechanization may result in excessive force being transmitted to the catheter.

Kinking can also occur during the infusion or use cycle. A typical cause of this failure is the placement of the catheter into tissue which undergoes significant movement during physical activity, which weakens the structure of the catheter, making the catheter less likely to resist mechanical forces that may bend or twist the catheter. Damage that causes deformation of the catheter may also contribute to kinking.

There are many advantages to flexible catheters, including ease of insertion into a patient, user comfort, and reasonable cost. However, there can also be some disadvantages. Flexible catheters are generally more susceptible to kinking than non-flexible catheters. The material used in most flexible catheters is a polymer, such as TEFLON® polymer. Such material provides flexibility to the catheter. However, the flexible nature of such catheters contributes to kinking because the walls of such catheters are not rigid and are therefore susceptible to deformation due to movement of the catheter and/or the patient.

Accordingly, a need exists for an improved catheter design and construction that will improve the functionality of the catheter while minimizing the disadvantages noted above. More specifically, a need exists to improve the design and construction of a flexible catheter that maintains its flexible characteristics without the negative aspects of the flexible design that contribute to kinking.

SUMMARY OF THE INVENTION

Objects of the present invention are to provide a flexible catheter configured and arranged to optimize column strength while maintaining or improving its flexible characteristics and tensile strength, and without adversely affecting its ability to be inserted into and removed from a patient.

These and other objects are substantially achieved by providing a flexible catheter having a swellable inner member surrounded by a non-swellable outer sleeve, in which the swellable inner member swells upon absorption of part of the infusate or other fluid that is administered through the catheter, to increase the wall strength of the catheter. This improves the catheter's resistance to kinking or other type of blockage, while the outward expansion of the inner member is constrained by the non-swellable outer sleeve. The improved catheter can be configured to optimize strength to avoid kinking and other undesirable complications, while permitting insulin or other medicaments to be administered via the catheter. The improved catheter can replace a conventional catheter without modification of the infusion set, insertion mechanism, or patch pump.

BRIEF DESCRIPTION OF THE DRAWINGS

The various objects, advantages and novel features of the present invention will be more readily appreciated from the following detailed description of exemplary embodiments thereof when read in conjunction with the appended drawings, in which:

FIG. 1A is a perspective view of an infusion set;

FIG. 1B is a top view of the infusion set of FIG. 1A;

FIG. 1C is a view of top view of the infusion set of FIG. 1A in which the line set is detached from the base;

FIG. 2 is a perspective view of an exemplary catheter of the present invention, before expansion of the inner member;

FIG. 3 is a perspective view of an exemplary catheter, after substantial inward expansion of the inner member;

FIG. 4 illustrates another perspective view of the catheter of FIG. 2 and a cross-sectional view thereof, before expansion of the inner member;

FIG. 5 illustrates another perspective view of the catheter of FIG. 2 and a cross-sectional view thereof, after substantial inward expansion of the inner member;

FIG. 6 is a perspective view of an introducer needle that is inserted into the catheter of FIG. 2;

FIG. 7 is an enlarged cross-sectional view of the catheter of FIG. 2 before expansion of the inner member;

FIG. 8A is an enlarged cross-sectional view of another catheter embodiment;

FIG. 8B is a view of the catheter of FIG. 8A illustrating certain dimensions;

FIG. 9A is a cross-sectional view of another exemplary catheter embodiment;

FIG. 9B is a cross-sectional view of another exemplary catheter embodiment, after the inner member has become swollen;

FIG. 10A is a cross-sectional view of another exemplary catheter embodiment;

FIG. 10B is a cross-sectional view of another exemplary catheter embodiment, after the inner member has become swollen;

FIG. 11A is a perspective view of a compression test that is conducted on the catheter of FIG. 2 by pressing the catheter between a probe and a base;

DETAILED DESCRIPTION OF THE EXEMPLARY EMBODIMENTS

Figure 1D:
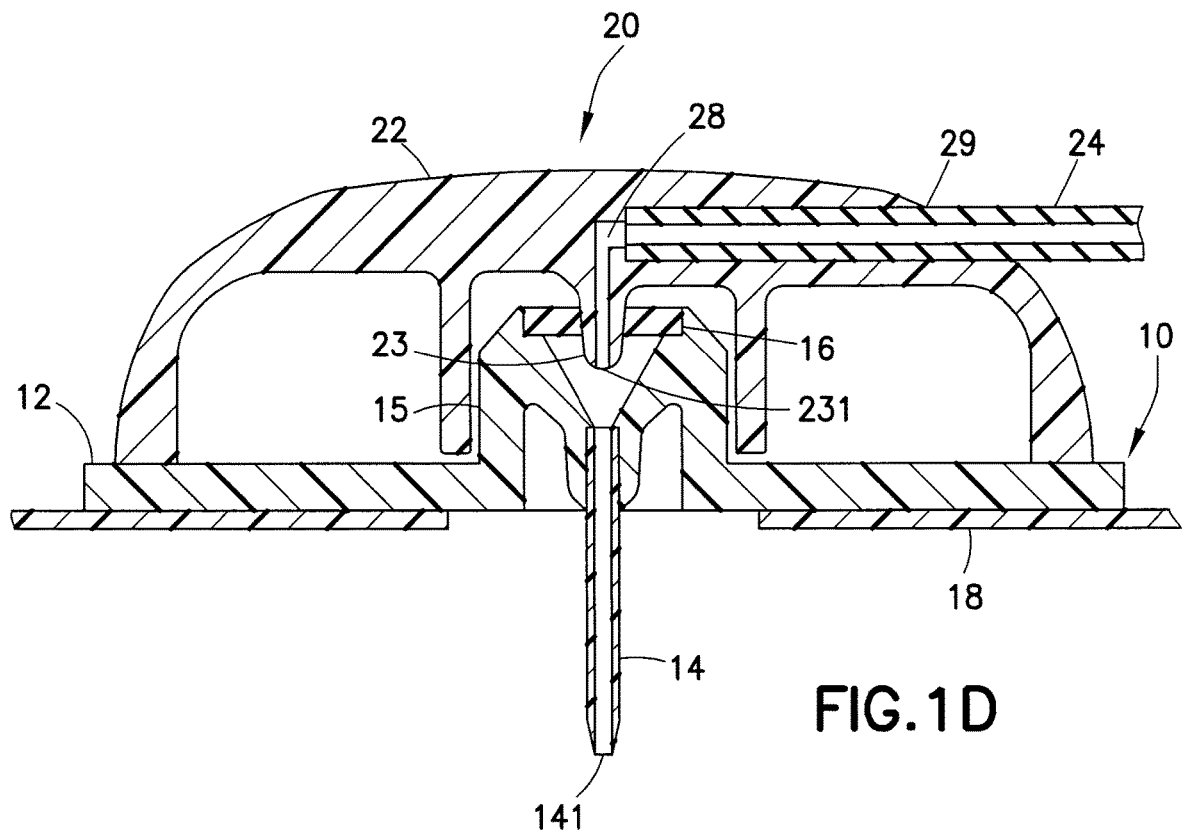
FIG. 1D is a cross-sectional view of the infusion set of FIG. 1A.
Figure 1E:
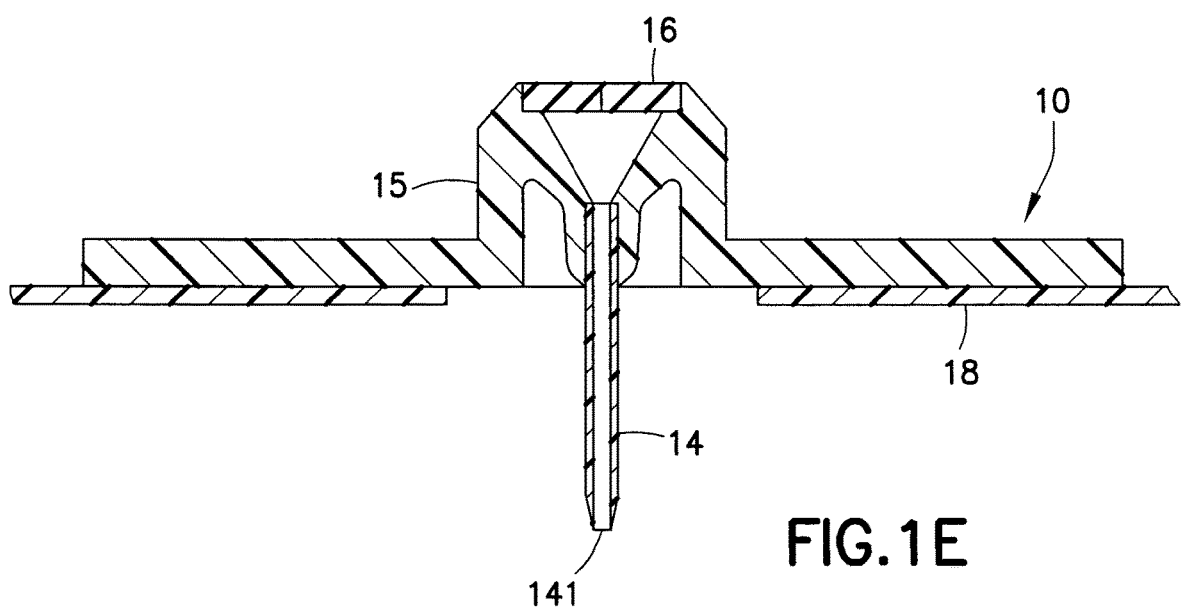
FIG. 1E is a cross-sectional view of the infusion set of FIG. 1D, after the hub 22 has been removed from the base.

Although reference will be made to the exemplary embodiments depicted in the drawings and the following descriptions, the embodiments disclosed herein are not meant to be exhaustive of the various alternative designs and embodiments that are encompassed by the present invention.

As illustrated in FIGS. 2-7, an exemplary embodiment of the present invention is a catheter 14a that can function in the same manner as the catheter 14 of FIGS. 1A and 1D. The catheter 14a is composed of (1) a swellable inner element in the form of an inner tube 100 that is preferably produced from a swellable polymer, and (2) an external, non-swellable outer sleeve 200 that is preferably produced from a non-swellable polymer. The swellable inner tube 100 can be replaced by structures other than a tube, as illustrated in FIGS. 10A and 10B. The non-swellable outer sleeve 200 is sized and shaped like the catheter 14 of FIGS. 1A and 1D.

In general, "swellable" in this context describes the ability of a material to absorb something, such as a liquid, and to swell in volume or size due to the absorption. Absorption or non-absorption of liquid can be targeted. For instance, one object may not be able to absorb a particular liquid due to its composition and/or configuration, while another object may be able to absorb the same liquid and swell in size or volume. Such properties are effectively utilized in the present invention.

The swellable inner tube 100 of FIGS. 2-7 is preferably produced from a swellable polymer, such as polyurethane. More particularly, a polyurethane product such as VIALON™ biomaterial by Becton, Dickinson and Company (BD) can be used to make the swellable inner tube 100 of FIGS. 2-7 or the swellable segments 100b of FIGS. 9A and 9B. The swellable inner tube 100 will absorb a part of the liquid infusate that is administered via the catheter, that it comes in contact with, to swell its volume. In an infusate containing insulin, VIALON™ biomaterial absorbs the liquid solution in which the insulin is suspended, and not the insulin itself. The liquid that is absorbed by the VIALON™ biomaterial is mostly water. The amount and rate of swelling of the swellable inner tube 100 can be controlled by formulating its composition and providing various structures to produce the desired characteristics. It is noted that insulin that is administered to a patient is typically in an aqueous solution with water content typically being in excess of 95%, and the water is more readily absorbed by the VIALON™ biomaterial.

For example, VIALON™ biomaterial can be formulated to control its degree of swelling by absorption of liquid so that it can swell in size or volume by 30% to 300%. Therefore, by careful selection of the material formulation, the amount, volume and rate of swelling of the swellable inner tube 100 can be controlled. For illustrative purposes, in embodiments of the present invention, the maximum swelling of the swellable inner tube 100 is set at approximately 60%, but can be varied for specific uses. Additional disclosures of the exemplary VIALON™ biomaterial can be found in commonly assigned U.S. Pat. Nos. 5,226,899 and 5,453,099 to Min-Shiu Lee et al., U.S. Pat. No. 5,545,708 to Theo Onwunaka et al., and U.S. Patent Application Publication No. 2011/0054390 to Gary Searle et al., the entire contents, disclosure and subject matter of each of the foregoing documents being expressly incorporated herein by reference. The VIALON™ biomaterial polymer provides compatibility with physiologic conditions, and VIALON™ biomaterial polymer has the added advantage of generally not requiring processing additives such as antioxidants and detackifiers that may be extractable and therefore undesirable in biomedical applications. VIALON™ biomaterial is a thermoplastic polyurethane, and therefore it can be thermoformed using techniques such as extrusion and injection molding.

The swellable inner tube 100 and the non-swellable outer sleeve 200 combine to form a catheter 14a that can function similarly to a conventional catheter in the delivery or infusion of insulin. Therefore, the catheter 14a can be substituted for the catheter 14 of FIG. 1D, in an infusion delivery set as illustrated in FIGS. 1A-1D, or in a patch pump.

When the catheter 14a is substituted for a conventional catheter in an insulin infusion set or patch pump, in order to attach or insert the catheter 14a to the patient, an introducer needle 50 is inserted into the swellable inner tube 100 of the catheter 14a, as illustrated in FIG. 6. The combined catheter 14a and introducer needle 50 are then inserted into the skin of the patient and the introducer needle 50 is withdrawn while the catheter 14a remains attached to the patient. This is similar to the conventional way of inserting a catheter of an insulin infusion set. During this process, the inner surface of swellable inner tube 100 may come in contact with the introducer needle 50, but the swellable inner tube 100 is dimensioned so that there will not be excessive interference with the introducer needle 50 to cause damage to the swellable inner tube 50 or to the overall catheter 14a.

The introducer needle shown in FIG. 6 may be a 27 g cannula, which has a diameter of 0.0163 in. The swellable inner tube 100 is sized and configured to accommodate the 27 g cannula. The inner diameter of the non-swellable outer sleeve 200 can be 0.0248 in, the thickness of the thinner segments 140 can be 0.002 in, and the thickness of the thicker segments 120 can be 0.004 in, which will accommodate the introducer needle 50.

Thereafter, insulin infusion or delivery to the patient via the catheter 14a takes place via the insulin infusion set (as illustrated in FIGS. 1A-1D, for example) as desired, required and/or programmed. Multiple infusions can take place before the catheter 14a becomes occluded due to some blockage caused by kinking or occlusion, after which the catheter 14a is detached from the patient and discarded.

It is noted that FIGS. 2-6 represent the catheter 14a as a tubular structure, for ease of explanation, but the end opposite to the distal opening 141 can be shaped to attach to an adapter (as in adapter 15 in FIGS. 1C and 1D). In other words, the catheter 14a can have the external shape of a conventional catheter. Unlike the catheter 14 of FIGS. 1C and 1D, however, catheter 14a includes a swellable inner tube 100.

When insulin infusion occurs, insulin is delivered to the patient via the swellable inner tube 100, which, due to its constituent material (e.g. VIALON™ biomaterial), is able to absorb a part of the infusate (mostly water) that is administered to the patient. The amount absorbed is negligible and does not affect the desired insulin therapy, especially since insulin is generally not absorbed. FIGS. 2 and 4 illustrate catheter 14a prior to absorption of any infusate by the swellable inner tube 100. Upon absorption of a part of the infusate, the swellable inner tube 100 swells both inwardly and outwardly, as illustrated in FIGS. 3 and 5. As illustrated in FIGS. 3 and 5, the outward swelling of the swellable inner tube 100 is restrained by the non-swellable outer sleeve 200. Since outward swelling is restrained by the non-swellable outer sleeve 200, the swelling or expansion of the swellable inner tube 100 is directed inward, as illustrated in FIGS. 3, 5 and 8-10.

It is also desirable to control the direction of swelling of the swellable inner tube 100, since uncontrolled expansion may cause discomfort to the patient and have other undesired consequences, such as creating bulges or weak points in the catheter 14a that may cause a rupture. In order to control the outward expansion of the swellable inner tube 100, an external, non-swellable outer sleeve 200 is positioned around the swellable tube 100, as illustrated in FIGS. 2-7. The external, non-swellable outer sleeve 200 can be made of a material that will not significantly swell by absorption of liquid, such as TEFLON® polymer or similar polymers. The non-swellable outer sleeve 200 can be friction-fit, fused or otherwise connected to the swellable inner tube 100 to form the catheter 14a. It is also possible for the swellable inner tube 100 and the non-swellable outer sleeve 200 to be made as a single unit, without assembling the two parts, via a co-extrusion process, for example.

The non-swellable outer sleeve 200, preferably made of TEFLON® polymer, will not significantly absorb liquid that it comes in contact with and will not significantly swell in size. The non-swellable outer sleeve 200 acts to restrain the outward swelling or expansion of the swellable inner tube 100, as the swellable inner tube 100 swells upon absorption of liquid of the infusate. The non-swellable outer sleeve 200 is configured to have sufficient strength to retain the outward swelling or expansion of the swellable inner tube 100. For example, the strength of the non-swellable outer sleeve 200 can be increased by increasing its thickness.

It should be understood that the terms "swellable" and "non-swellable" are used in a relative and not absolute sense. For, example, the non-swellable outer sleeve 200 can experience a small degree of swelling when exposed to infusate or body fluids, or even due to heat, as long as the amount of such swelling is small enough to allow the outer sleeve 200 to restrain the outward swelling of the swellable inner tube 100 as discussed above. In other words, the outer sleeve 200 can be somewhat swellable as long as it is less swellable than the inner tube 100. And, conversely, the inner tube 100 need not be swellable to a great degree as long as it is more swellable than the outer sleeve 200.

As illustrated in FIG. 7, the non-swellable outer sleeve 200 is preferably a thin-walled structure such as TEFLON® polymer shrink tubing with a wall thickness of approximately 0.0005 inch, which is the difference between the inner diameter D1 and the outer diameter D2 of the non-swellable outer sleeve 200. The outer diameter D2 and the inner diameter D1 of the outer sleeve may be 0.026 in and 0.025 in, respectively. The non-swellable outer sleeve 200 is configured to restrain the outward expansion of the swellable inner tube 100 and related expansion forces, shown as arrows in FIG. 7. For such purpose, TEFLON® polymer shrink tubing of different thicknesses can be used for the outer sleeve 200. TEFLON® polymer shrink tubing is commercially available having a thickness as low as 0.00025 inch, and such shrink tubing can be used to form the external non-swellable outer sleeve 200.

When insulin treatment is started, infusate containing insulin is pumped into the catheter 14a, and the swellable inner tube 100 beings to swell as liquid of the infusate is absorbed. The non-swellable outer sleeve 200 prevents outward swelling or outward expansion of the swellable inner tube 100, from the perspective of the centerline of the catheter 14a, the swelling or expansion of the swellable inner tube 100a is directed inwardly, toward the centerline of the catheter 14a and circumferentially along the inner diameter D1 of the non-swellable outer sleeve 200, in the directions of the arrows of FIG. 7.

The direction of swelling of the inner tube 100 can be controlled by configuring the swellable inner tube 100 to include alternating thicker segments 120 and thinner segments 140 and indents 142 on the thinner segments 140, as illustrated in FIGS. 2 and 7. As the swellable inner tube 100 swells in size, the thinner segments 140 become folded inwardly at their respective indents 142, toward the centerline of the catheter 14a to form internal support legs 146, as illustrated in FIGS. 3 and 5. The formation of the internal support legs 146 as the thinner segments 140 and thicker segments 120 swell in size increases the structural strength of the catheter 14a. The indents 142 may run along the length of the thinner segments 140, as illustrated in FIG. 2, and one or more indents may be formed on the inner and/or outer surfaces of the swellable inner tube 100 to control the manner and direction of the swelling of the inner tube 100. The swelling or growth of the thicker segments 120 influences the movement and folding of the thinner segments 140 to form the internal support legs 146.

In addition, the swelling of the swellable inner tube 100 toward the centerline of the catheter 14a and circumferentially along the inner diameter D1 of the non-swellable outer sleeve 200 is controlled so that the catheter orifice 160 formed along the inner surface of the swellable inner tube 100 remains open in order to permit infusate to be pumped into the catheter 14. When the inner tube 100 swells to its maximum size by the absorption of liquid infusate and/or body fluids it comes in contact with, as illustrated in FIGS. 3 and 5, even though the cross-section of the catheter orifice 160 has become reduced, the orifice 160 remains open so that insulin infusion can take place via the swellable inner tube 100, without triggering a blockage or back pressure alarm.

In the catheter embodiment illustrated in FIGS. 1-7, as more clearly illustrated in FIG. 7, the cross-section of the swellable inner tube 100 has six segments that resemble a hexagon. There are three thicker segments 120 alternately located between three thinner segments 140. The thinner segments 140 have been further thinned or weakened at specific locations, at indents 142, to control the movement of the segments 120, 140 during swelling, and so that the thinner segments 140 fold inwardly at the indents 142 to form internal support legs 146. The segments 120, 140 and indents 142 preferably run substantially continuously and uniformly along the length of the swellable inner tube 100. Although a hexagonal arrangement for the swellable inner tube 100 is illustrated, there can be more or less sides, while maintaining the objectives of strengthening the structural integrity of the overall catheter 14a and maintaining a sufficient catheter opening or orifice 160 to permit insulin therapy, as the inner tube 100 swells in size.

FIGS. 8A and 8B illustrate cross-sectional views of another exemplary catheter embodiment of the present invention. Catheter 14b of FIGS. 8A and 8B is similar to the catheter 14a of FIGS. 2-7 and uses a swellable inner element in the form of an inner tube 100a. However, the swellable inner tube 100 of FIG. 7, the swellable inner tube 100a of the catheter 14b includes thicker segments 120a each having a concave surface 122 customized to accommodate an outer surface of the introducer needle 50. Such an arrangement can accommodate more swellable material in the inner tube 100a, as illustrated in FIG. 8A. Parts of the cylindrical outer surface of the introducer needle 50 are received at the reciprocally shaped concave surfaces 122 of the thicker segments 120a, as illustrated in FIG. 8A. The thinner segments 140 of the swellable inner tube 100a may also contact the introducer needle 50, as illustrated in FIG. 8A. As the thinner segments 140 can be made to be sufficiently thin and flexible so that they may be pushed slightly outwardly by the introducer needle 50. In addition, indents 142 on the thinner segments 140 may be configured to reduce the resistance of the thinner segments 140 to the introducer needle 50.

FIG. 8B illustrates the catheter 14b without the introducer needle 50. Exemplary dimensions for the catheter 14b are provided as follows. As illustrated in FIG. 8A, the outer diameter D1 of the non-swellable outer tube 200 is 0.026 in, and the wall thickness T1 of the outer tube 200 is 0.0005 in. As illustrated in FIG. 8B, the wall thickness T2 of each of the thinner segments 140 is 0.002 in, which is further reduced where indents 142 are present. The wall thickness of the thicker segments 120 varies as they conform to the inner diameter of the outer sleeve 200 as illustrated in FIG. 8B, but the thickness T3 of the thicker segments 120 is 0.004 in. With further regard to each of the thicker segments 140, the radius R1 of its outer wall is 0.012 in and the radius R2 of its inner wall is 0.008 in at the concave surface 122, which provides a thickness of 0.004 in. In addition, the rotational angle A1 of each of the thinner segments 140 can be set at 45 degrees and the rotational angle A2 of each of the thicker segments 120 can be 75 degrees, as illustrated in FIG. 8B to correspond to 60% expansion in the swellable material.

Figure 8C:
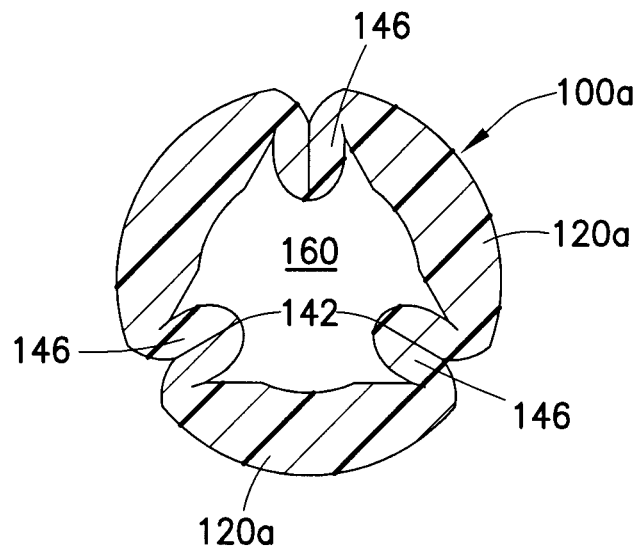
FIG. 8C is an enlarged cross-sectional view of the inner member of the catheter of FIG. 2, with the inner member shown partially swollen.
Figure 8D:
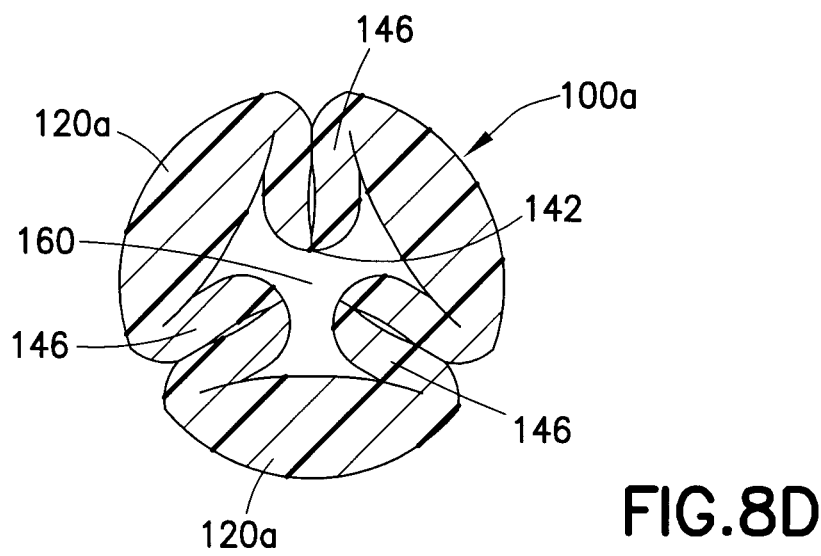
FIG. 8D is an enlarged cross-sectional view of the inner member of the catheter of FIG. 2, with the inner member shown fully swollen.
Figure 8E:
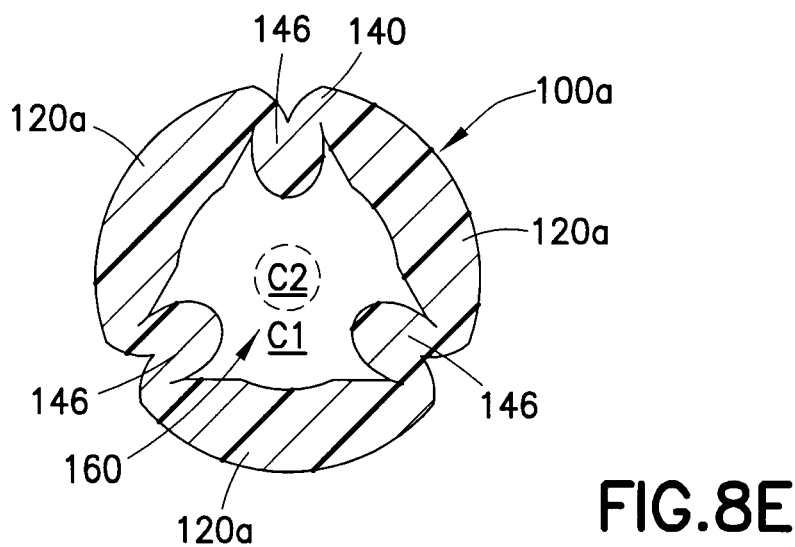
FIG. 8E is an enlarged cross-sectional view of the inner member of the catheter of FIG. 8A, illustrating the size of the internal lumen relative to that which would trigger a pump occlusion alarm.

FIGS. 8C, 8D and 8E illustrate a cross-section of the embodiment of FIGS. 8A and 8B without showing the non-swellable outer tube 200. However, it is noted that the actual swelling of the inner tube 100a takes place within non-swellable outer sleeve 200. FIG. 8C illustrates an initial swelling of the inner tube 100a, after the thinner segments 140 have folded to form the internal support legs 146. FIG. 8D illustrate the inner tube 100a after it has completely swelled in size and cannot swell any further. In FIG. 8D, the internal support legs 146 and the thicker segments 120 have increased in size to reduce the orifice 160.

FIG. 8D illustrates the swellable inner tube 100a after swelling approximately 60% in size. FIG. 8D illustrates the inner tube 100a after maximum absorption of insulin has taken place, while maintaining the opening for the catheter orifice 160 that is sufficient to administer insulin via the swellable inner tube 100a of the catheter 14b. The controlled swelling of the swellable inner tube 100a and its interface with the external non-swellable outer sleeve 200 improves the structural integrity of the catheter 14a, 14b and to resist external forces that contribute to catheter collapse, kinking or pinching.

In developing the present invention, analysis was conducted to determine the increase in back pressure at the infusion pump resulting from increasing degrees of occlusion or blockage of the inner diameter of the catheter. As the swellable inner tube 100a swells in size due to liquid absorption, the orifice 160 is reduced in size as it is displaced by the swelling of the inner tube 100a. The analysis indicated that even a 60% reduction in the cross-sectional area of the catheter orifice 160 resulted in only a minimal increase of 4 psi (pounds per square inch) in back pressure at the infusion pump.

In the example illustrated in FIG. 8E, the swellable inner catheter is made of 60% swellable VIALON™ biomaterial and is shown with a catheter orifice 160 (the area inside the inner tube 100a) having a cross-sectional area C1 of 0.00016076 in$^2$. After undergoing maximum swelling and fully forming the supportive, internal support legs 146, as illustrated in FIG. 8D, the reduction in cross-sectional area of the catheter orifice 160 is only 42%, and the uncompressed lumen space is much larger than the 0.0000241 in$^2$ cross-sectional area C2 (the area inside the innermost circle) illustrated in FIG. 8E, that would result in the pump pressure increasing to where the pump would trigger an occlusion alarm or cause a loss of infusion therapy.

FIGS. 9A and 9B illustrate another embodiment of the inventive catheter. As illustrated in FIG. 9A, the catheter 14c includes an inner member in the form of a swellable inner tube 100b. The swellable inner tube 100b can be a composite structure with three main swellable segments 125, equally spaced around the inner diameter of the non-swellable outer sleeve 200, and thin connective segments 145 that connect the adjacent main swellable segments 145. The catheter orifice 160 includes lateral orifices 161 that are formed between the main swellable segments 125. The main swellable segments 125 include leading surfaces 126 that will accommodate an introducer needle therebetween.

After the swellable inner tube 100b absorbs liquid from the infusate and has swollen in size, as illustrated in FIG. 9B, the inner tube 100b swells in size and catheter orifice 160, including the lateral orifices 161, is reduced in size but remains open. The leading surfaces 126 of each of the main swellable segments 125 also increase in size such that they cannot fit into the opposing lateral orifices 161. As described in the other embodiments, the main swellable segments 125 and the thin connective segments 145 can be thinned or weakened at specific locations to control the motion of expansion or swelling, and/or cause folding, as swellable inner tube 100b swells as liquid from the infusate is absorbed.

FIGS. 10A and 10B illustrate another embodiment of the inventive catheter. In the catheter 14d, there is no inner swellable tube, as in the other embodiments. Instead, the inner member comprises swellable segments 105 made of a swellable material such as VIALON™ biomaterial that are not initially interconnected, as illustrated in FIG. 10A. The swellable segments 105 each include a thicker segment 125 and a pair of thin segment legs 145. The swellable segments 105 can be attached to the inner walls of the non-swellable outer sleeve 200a by various means. As illustrated in FIGS. 10A and 10B, the non-swellable outer sleeve 200a includes retention tabs 210 on to which the swellable segments 105 are attached. The swellable segments 105 and the outer sleeve 200a having retention tabs 210 can be coextruded to form the catheter 14d and cut to required lengths.

As the swellable segments 105 swell in size, adjacent ones of the thin segment legs 145 swell and fold inwardly toward the orifice 160, as illustrated in FIG. 10B. The swelling of the thicker segments 125 also urge the folding movement of the thin segment legs 145 and form a cross-section similar to the embodiments that are illustrated in FIGS. 3 and 8D. Even after the swellable segments 105 have completely swelled in size, the catheter orifice or lumen 160 remains open to allow uninterrupted infusion therapy, while increasing the structural integrity of the catheter 14d. In addition, as described in the other embodiments, the swellable segments 105 can be thinned or weakened at specific points to control the motion of expansion or swelling, and/or cause folding, such that the composite structure can form a customized cross-section, after swelling is complete.

Figure 11B:
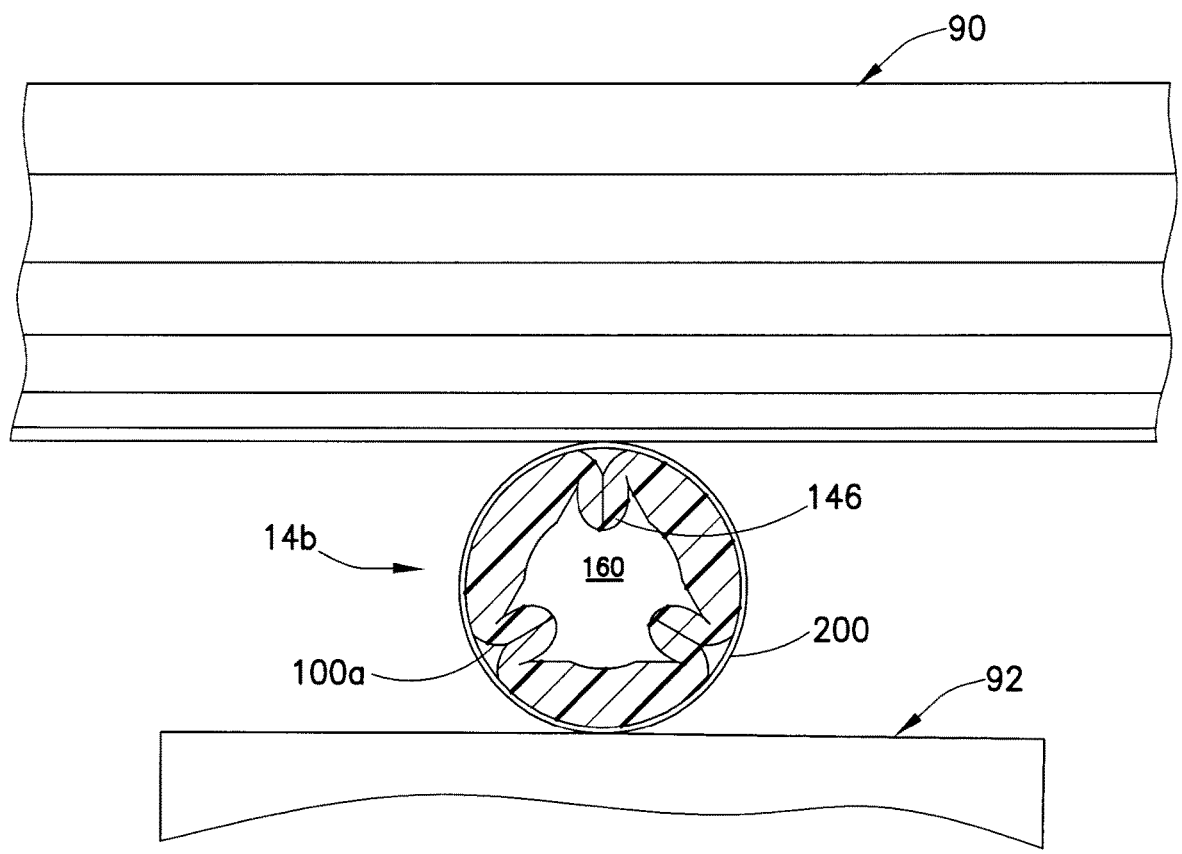
FIG. 11B is a cross-sectional view of the catheter of FIG. 2 with a partially swollen inner member, prior to a compression test.
Figure 11C:
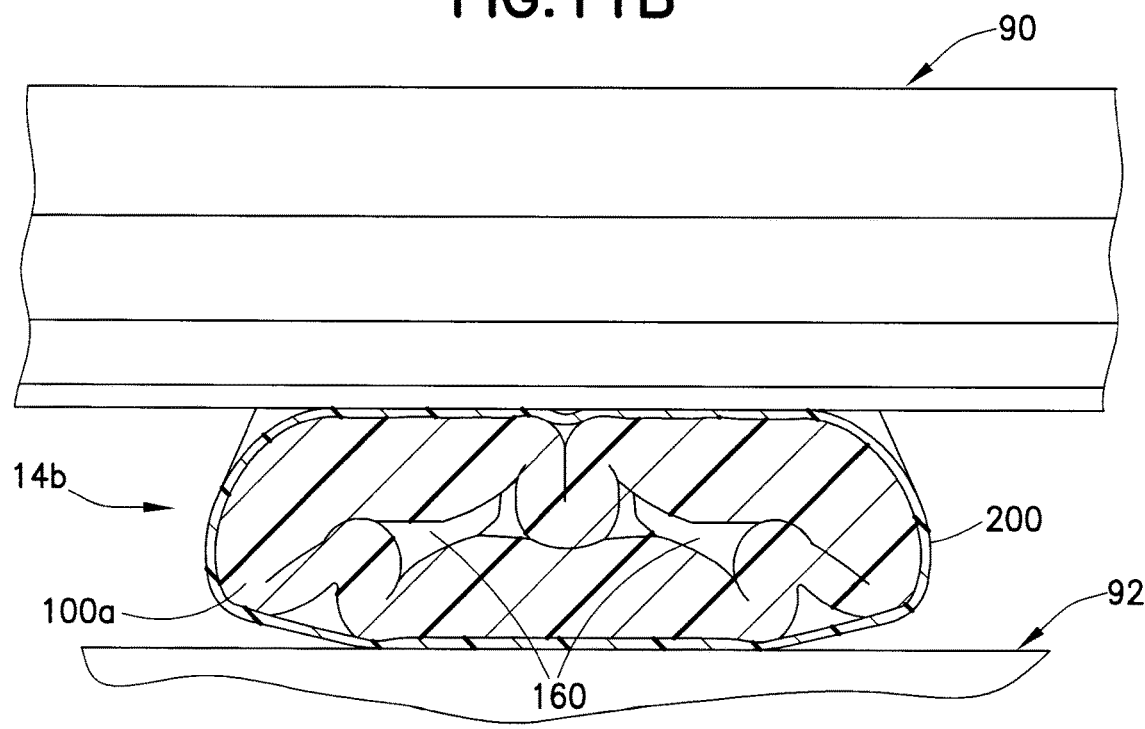
FIG. 11C is a cross-sectional view of the catheter of FIG. 11B during the compression test.

FIG. 11A illustrates a finite element analysis (FEA) in which the catheter 14b of FIG. 8A was subjected to simulated compression tests to compare the force required to compress the inventive catheter 14b, as compared with a conventional catheter. In the FEA simulations, the catheter 14b was placed on a base 92 and a probe 90 was pressed on the catheter 14b at various stages of swelling of the swellable inner tube 100, to view the resistance to the compression by the catheter 14b. FIG. 11B illustrates the catheter 14b, with the inner swellable inner tube 100a that has swollen in size such that the cross-sectional area of the catheter orifice 160 has been reduced to about 42% of its original size, prior to compression by the probe 90. FIG. 11C illustrates the catheter 14*b* after a set compression force has been applied. The thickened walls of the swellable inner tube 100, due to swelling, and the configuration of the components thereof, such as the thicker and thinner segments 120*a*, 140 and the formation of the internal support legs 146, resisted total collapse and maintained an opening of the catheter orifice 160 sufficient to administer insulin therapy.

Figure 11D:
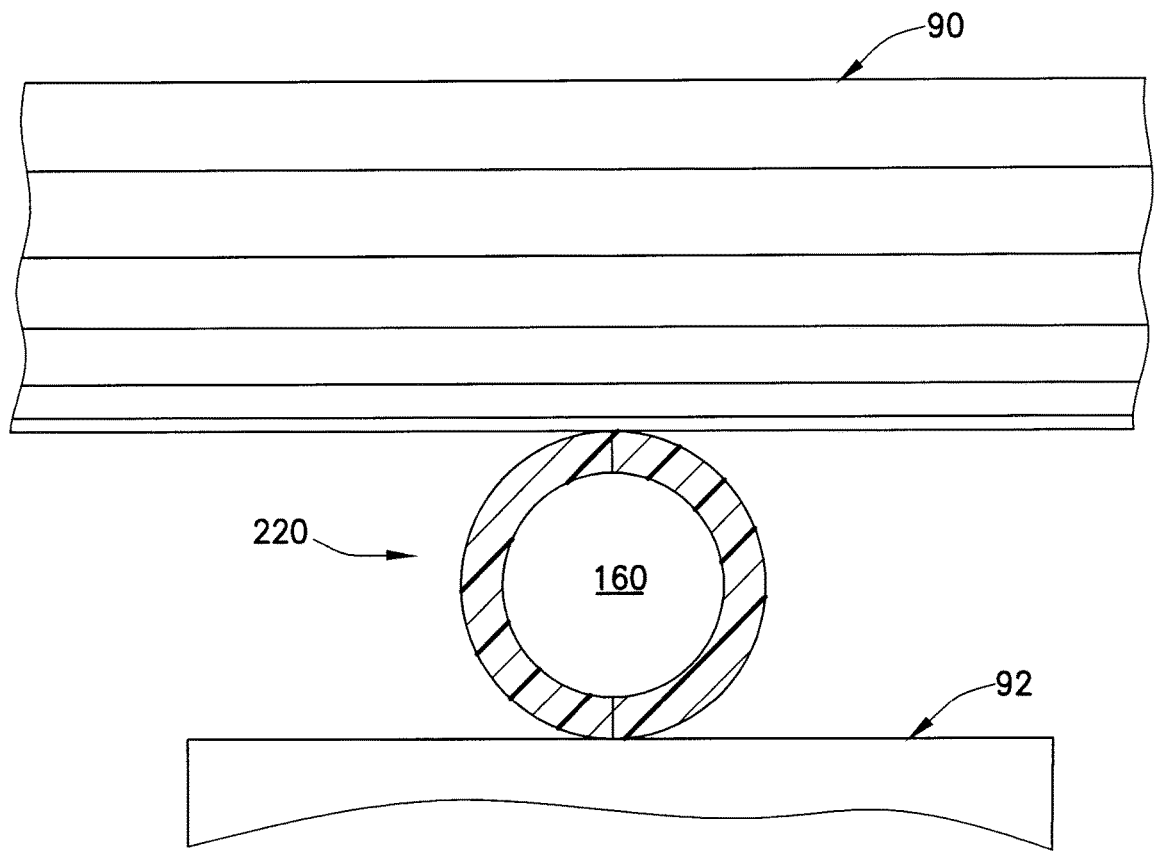
FIG. 11D is a cross-sectional view of a conventional catheter, prior to a compression test.
Figure 11E:
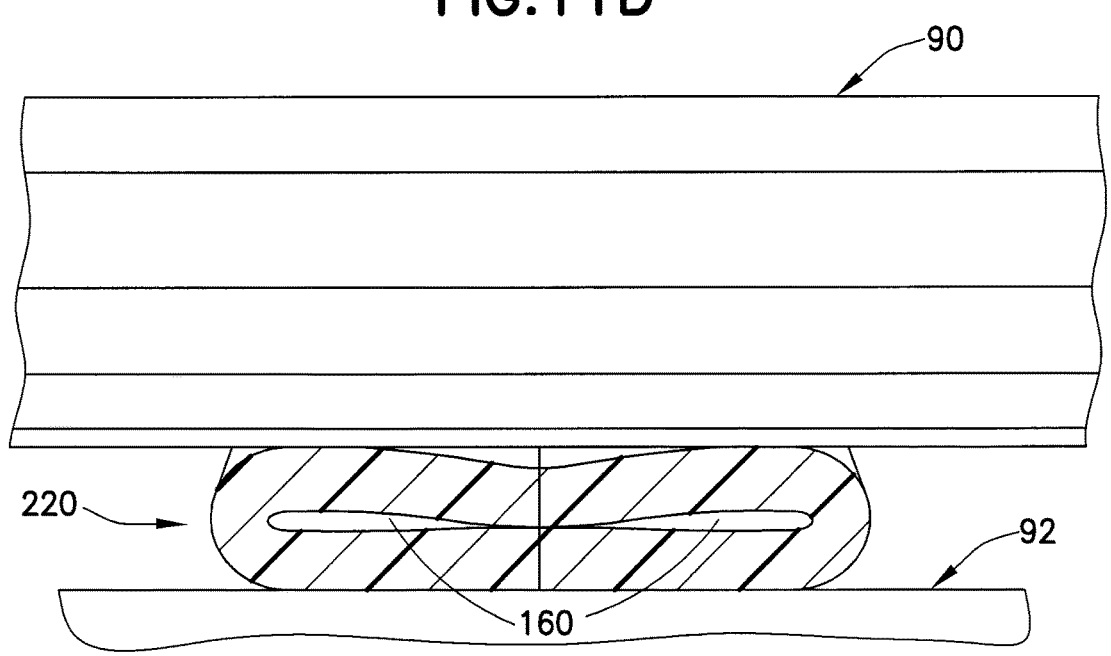
FIG. 11E is a cross-sectional view of the catheter of FIG. 11B during the compression test.

In comparison, FIG. 11D illustrates a conventional catheter 220, before the application of the same set compression force in an FEA simulation. FIG. 11E illustrates the conventional catheter 220 after the set compression force has been applied. The conventional catheter 220, having no internal support structures like the catheter 14*b*, failed to resist the compression, resulting in a near-total collapse of the catheter orifice 160, which would have triggered an occlusion alarm if such collapse occurred during infusion therapy. The compression force simulates conditions which the catheter may be subjected to that would cause kinking and/or occlusion.

The finite element analysis indicated that the inventive catheter 14*b* can be expected to withstand approximately double the amount of force than a conventional catheter 220 before triggering an occlusion alarm. The force required to pinch to a minimum area before an occlusion alarm can be triggered for the conventional catheter 22 was 0.334 lb., while the force required to pinch to a minimum area for the inventive catheter 14*b* was 0.660 lb.

The manufacture and assembly of the catheter 14*a*, 14*b* of the present invention will now be further described. A one-part swellable inner tube 100, 100*a* can be produced from a continuous extrusion process that is well known in the art. The external non-swellable outer sleeve 200 can also be produced from a continuous extrusion process. The external non-swellable outer sleeve 200 can be produced from a medical grade TEFLON® polymer shrink tubing that can be manufactured with an inner diameter slightly larger than the outer diameter of the swellable inner tube 100, 100*a*, in order to allow the two pieces to be assembled together to allow a slip-fit assembly of the catheter 14*a*, 14*b*. The entire non-swellable outer sleeve 200 can be shrunk in diameter, or just the lead end of the non-swellable outer sleeve 200 can be shrunk in diameter, to bind the two components to form the catheter 14*a*, 14*b*. Thereafter, the two-part assembly can be completed by Radio Frequency (RF) tipping to further bond the lead end of the external non-swellable outer sleeve 200 to the swellable inner tube 100, 100*a*. Alternately, the swellable inner tube 100, 100*a* can be molded to a finished length and tip dimensions, and the external non-swellable outer sleeve 200 can be attached as described above. A similar process can form the catheter 14*d* of FIGS. 10A and 10B.

With regard to the composite catheter 14*c* of FIGS. 9A and 9B, the swellable inner tube 100*b* and the external non-swellable outer sleeve 200 can be continuously extruded and/or co-extruded, using conventional processes. TEFLON® polymer shrink tubing can be used to make the external non-swellable outer sleeve 200. The swellable segments 125, 145 of the swellable inner tube 100*b* and the non-swellable outer sleeve 200 can be co-extruded and cut to desired lengths.

The swellable inner tube 100, 100*a*, 100*b* and the swellable segments 105 can be co-extruded or two-shot molded, and the external non-swellable outer sleeve 200 can be attached to the swellable tube 100, 100*a*, 100*b* or swellable segments 105 by the methods described above. The composite catheter 14*c* of FIGS. 9A and 9B can be composed of a non-swellable sleeve that is over-molded or co-extruded with segments of swellable polymer.

There are numerous advantages and improvements of the inventive catheter, citing catheter 14*b* as an example, over the conventional art. After the swellable inner tube 100*a* becomes swollen, the overall structure of the catheter 14*b* is able to resist or minimize kinking, because the internal support legs 146 that are formed as a result of the material swelling resist total collapse of the overall structure. At the same time, the flow of insulin is possible through the catheter orifice 160. Even though the cross-section of the catheter orifice 160 is reduced due to material swelling, a sufficient opening is maintained, such that the required pump pressure will not exceed the normal flow conditions of the pump and trigger an occlusion alarm.

Another advantage is that the inventive kink-resistant catheter 14*b* is potentially less expensive to produce than other anti-kinking catheter structures, such as in-dwelling flexible stainless steel needles or partially retracting introducer needles. Such alternative stainless steel needles are more rigid and can cause greater discomfort to the patient.

Another advantage of the inventive device is that the overall dimensions and gauge sizes of the collapse-resistant catheter 14*b*, including the swellable inner tube 100*a* and the non-swellable outer sleeve 200, conform to the gauge sizes currently used for insulin infusion, such as a 24 gauge introducer needle and a 27 gauge catheter. In other words, the catheter 14*b* can be substituted for a conventional catheter used in insulin infusion sets, without major modification. The advantages mentioned above, with regard to catheter 14*b* can generally be said of catheters 14*a*, 14*c* and 14*d*, as well.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. An infusion system comprising:
 a base;
 a pump;
 a fluid tubing set that connects the pump and the base; and
 a collapse-resistant catheter extending from the base and comprising:
  a swellable inner element including a swellable segment and a connective segment forming a catheter orifice; and
  a non-swellable flexible outer sleeve covering an outer wall of the inner element;
 wherein when the swellable inner element absorbs liquid, the swellable inner element swells in volume within the non-swellable flexible outer sleeve, the swellable segment increases in size, the connective segment folds, and the catheter orifice decreases in size while remaining open.

2. The infusion system as claimed in claim 1, further comprising a hub connected to the fluid tubing set and detachably connected to the base.

3. The infusion system as claimed in claim 1, wherein outward swelling of the inner element is externally restrained by the flexible outer sleeve.

4. The infusion system as claimed in claim 1, wherein the swelling of the inner element is directed inward toward its centerline.

5. The infusion system as claimed in claim 1, wherein the inner element comprises an inner tube.

6. The infusion system as claimed in claim 1, wherein the swellable segment includes a concave surface.

7. The infusion system as claimed in claim 1, wherein the connective segment is disposed on a side of the swellable segment.

8. The infusion system as claimed in claim 1, wherein the connective segment is configured to collapse toward the centerline of the collapse-resistant catheter, as liquid is absorbed.

9. The infusion system as claimed in claim 1, wherein the base comprises a flat surface.

10. The infusion system as claimed in claim 1, wherein the base comprises an adhesive that retains the base on the skin surface during use.

11. The infusion system as claimed in claim 1, wherein the connective segment swells when the swellable inner element absorbs liquid.

12. A patch pump comprising:
a housing;
a pump in the housing; and
a collapse-resistant catheter comprising:
    a swellable inner element including one or more indents a swellable segment and a connective segment forming a catheter orifice; and
    a non-swellable flexible outer sleeve covering an outer wall of the inner element;
wherein when the swellable inner element absorbs liquid, the swellable inner element swells in volume within the non-swellable flexible outer sleeve, the swellable segment increases in size, the connective segment folds, and the catheter orifice decreases in size while remaining open.

13. The patch pump as claimed in claim 12, wherein outward swelling of the inner element is externally restrained by the flexible outer sleeve.

14. The patch pump as claimed in claim 12, wherein the swelling of the inner element is directed inward toward its centerline.

15. The patch pump as claimed in claim 12, wherein the inner element comprises an inner tube.

16. The patch pump as claimed in claim 12, wherein the swellable segment includes a concave surface.

17. The patch pump as claimed in claim 12, wherein the connective segment is disposed on a side of the swellable segment.

18. The patch pump as claimed in claim 12, wherein the connective segment is configured to collapse toward the centerline of the collapse-resistant catheter as liquid is absorbed.

19. A collapse-resistant catheter comprising:
an inner element including a swellable segment and thin a connective segment forming a catheter orifice; and
a flexible outer sleeve covering an outer wall of the inner element; wherein
the inner element comprises a swellable material;
the flexible outer sleeve comprises a non-swellable material; and
when the inner element absorbs a portion of the liquid, the inner element swells in volume within the flexible outer sleeve, the swellable segment increases in size, the connective segment folds, and the catheter orifice decreases in size while remaining open.

20. A collapse-resistant catheter comprising:
a plurality of disconnected inner elements each including a swellable segment and a connective segment;
a flexible outer sleeve covering and being fixed to an outer wall of each of the plurality of inner elements; and
retention tabs on an inner surface of the outer sleeve that attach to an outer surface of the swellable segment; wherein
the inner element comprises a swellable material;
the flexible outer sleeve comprises a non-swellable material; and
when the inner element absorbs a portion of the liquid, the inner element swells in volume within the flexible outer sleeve, and the connective segment folds inwardly.

* * * * *